(12) United States Patent
Savchuk et al.

(10) Patent No.: US 8,309,559 B2
(45) Date of Patent: Nov. 13, 2012

(54) (EN) SUBSTITUTED 2-AMINO-3-SULFONYL-PYRAZOLO[1,5-A] PYRIMIDINES/ANTAGONISTS OF SEROTONIN 5-HT6 RECEPTORS, METHODS FOR THE PRODUCTION AND THE USE THEREOF

(76) Inventors: Nikolay Filippovich Savchuk, Rancho Santa Fe, CA (US); Alexander Vasilievich Ivashchenko, Calle Rancho Vista, CA (US)

( * ) Notice: Subject to any disclaimer, the term of this patent is extended or adjusted under 35 U.S.C. 154(b) by 0 days.

(21) Appl. No.: 12/812,733

(22) PCT Filed: Jan. 23, 2009

(86) PCT No.: PCT/IB2009/050272
§ 371 (c)(1),
(2), (4) Date: Jul. 13, 2010

(87) PCT Pub. No.: WO2009/093208
PCT Pub. Date: Jul. 30, 2009

(65) Prior Publication Data
US 2010/0292245 A1    Nov. 18, 2010

(30) Foreign Application Priority Data

Jan. 24, 2008  (RU) .................................. 2008102154
May 7, 2008   (RU) .................................. 2008117846

(51) Int. Cl.
*A01N 43/90*   (2006.01)
*A61K 31/519*  (2006.01)
*C07D 487/00*  (2006.01)

(52) U.S. Cl. ..................................... 514/259.3; 544/281
(58) Field of Classification Search ........................ None
See application file for complete search history.

(56) References Cited

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*

* cited by examiner

*Primary Examiner* — Jeffrey Murray

(57) ABSTRACT

The present invention relates to novel substituted 2-amino-3-(arylsulfonyl)pyrazolo[1,5-a]pyrimidines of general formula 1, to serotonin 5-HT$_6$ receptor antagonists, to novel drug substances and pharmaceutical compositions, to medicaments, methods for preparation thereof, and to methods for prophylaxis and treatment of various CNS diseases, pathogenesis of which is associated with disturbance of monoaminergic signaling pathways, more specifically over- or hypoactivation of serotonin 5-HT$_6$ receptors.

In general formula 1

Ar represents optionally substituted aryl or optionally substituted heterocyclyl; $R^1$ and $R^3$ independently of each other represent $C_1$-$C_3$ alkyl or aryl; $R^2$ represents hydrogen or $C_1$-$C_3$ alkyl; $R^4{}_1$, and $R^4{}_2$ independently of each other represent hydrogen, optionally substituted $C_1$-$C_3$ alkyl or optionally substituted phenyl, or $R^4{}_1$, and $R^4{}_2$ together with nitrogen atom they are attached to form optionally substituted heterocyclyl.

5 Claims, 1 Drawing Sheet

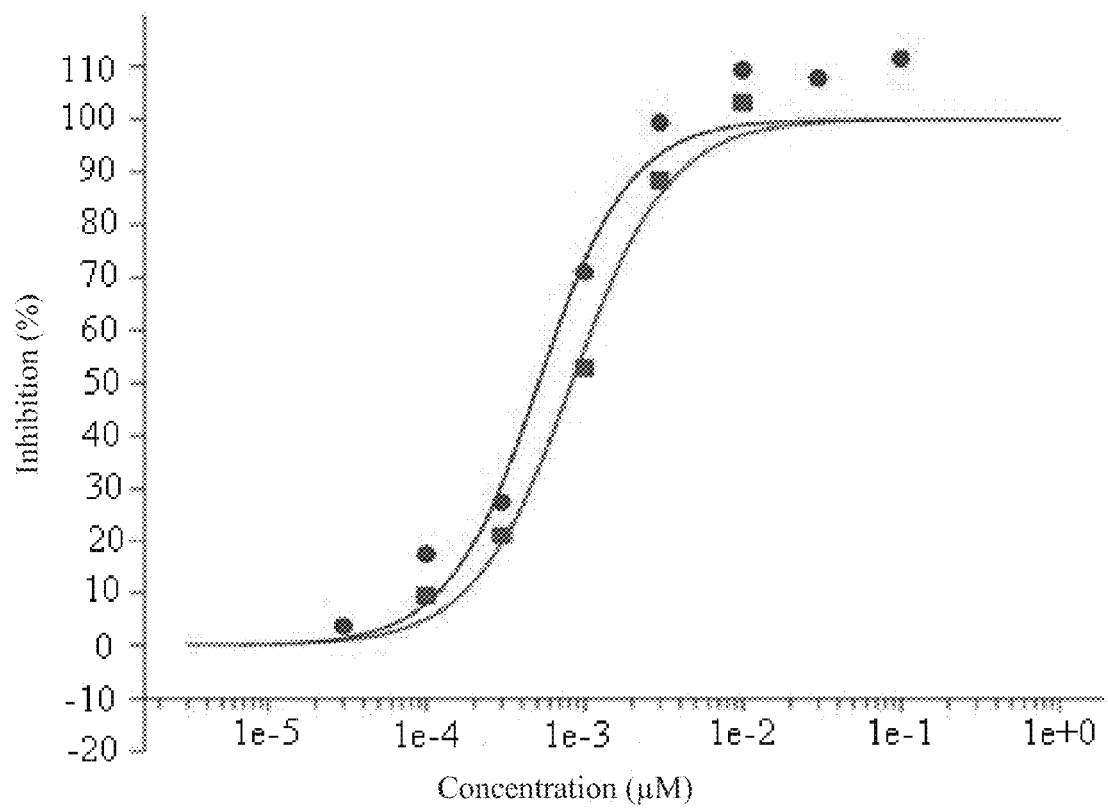

(EN) SUBSTITUTED 2-AMINO-3-SULFONYL-PYRAZOLO[1,5-A] PYRIMIDINES/ANTAGONISTS OF SEROTONIN 5-HT6 RECEPTORS, METHODS FOR THE PRODUCTION AND THE USE THEREOF

FIELD OF THE INVENTION

The invention relates to novel (arylsulfonyl)pyrazolo[1,5-a]pyrimidines, novel serotonin 5-$HT_6$ receptor antagonists, to novel drug substances, pharmaceutical compositions, medicaments, methods for their preparation and use. More specifically, the invention relates to serotonin 5-$HT_6$ receptor antagonists-substituted 2-amino-3-(sulfonyl)pyrazolo[1,5-a] pyrimidines, to drug substances, to pharmaceutical compositions, comprising the said compounds as active ingredients, and to methods of treatment and prophylaxis of various cognitive and neurodegenerative diseases. The origin of pharmacological effect of novel drug substances is their ability to interact with serotonin 5-$HT_6$ receptors playing the key role in treatment of central nervous system diseases (CNS), in particular, Alzheimer's disease (AD), Huntington's disease, schizophrenia, other neurodegenerative diseases, cognitive disorders and obesity.

BACKGROUND OF THE INVENTION

Usefulness of selective antagonists of serotonin 5-$HT_6$ receptors for treating of CNS diseases, in particular, schizophrenia, AD and other neurodegenerative diseases and cognitive disorders was proved conclusively in clinical practice and is regarded to be very perspective in medicine of future [Holenz J., Pauwels P. J., Diaz J. L., Merce R., Codony X., Buschmann H. Medicinal chemistry strategies to 5-$HT_6$ receptor ligands as potential cognitive enhancers and antiobesity agents. *Drug Disc. Today.* 2006; 11:283-299].

At mammals these receptors are localized exclusively in central nervous system (CNS), and mainly in parts of brain responsible for training and memory [Ge'rard C., Martres M.-P., Lefe'vre K., Miguel M.-C., Verge' D., Lanfumey L., Doucet E., Hamon M., El Mestikawy S. Immuno-localization of serotonin 5-$HT_6$ receptor-like material in the rat central nervous system. *Brain Research.* 1997; 746:207-219].

Besides, it was shown [Dawson L. A., Nguyen H. Q., Li P. The 5-HT(6) receptor antagonist SB-271046 selectively enhances excitatory neurotransmission in the rat frontal cortex and hippocampus. *Neuropsychopharmacology.* 2001; 25:662-668], that 5-$HT_6$ receptors are modulators of the whole number of neuromediator systems including cholinergic, noradrenergic, glutamatergic and dopaminergic. Taking into account the fundamental role of these systems in normal cognitive processes and their dysfunction at neurodegeneration, exclusive role of 5-$HT_6$ receptors in forming normal and "pathological" memory becomes obvious.

It was shown in a large number of nowadays publications that blocking of 5-$HT_6$ receptors leads to considerable enhancement of memory consolidation in various animal models of training-memorizing-reproduction [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29:93-100. Riemer C., Borroni E., Levet-Trafit B., Martin J. R., Poli S., Porter R. H., Bos M. Influence of the 5-HT6 receptor on acetylcholine release in the cortex: pharmacological characterization of 4-(2-bromo-6-pyrrolidin-1-ylpyridine-4-sulfonyl)phenylamine, a potent and selective 5-$HT_6$ receptor antagonist. *J. Med. Chem.* 2003; 46:1273-1276. King M. V., Woolley M. L., Topham I. A., Sleight A. J., Marsden C. A., Fone K. C. 5-HT6 receptor antagonists reverse delay-dependent deficits in novel object discrimination by enhancing consolidation e an effect sensitive to NMDA receptor antagonism. *Neuropharmacology* 2004; 47:195-204]. It was also demonstrated that considerable enhancement of cognitive functions in aged rats in Morrison's water maze experiment took place under the action of 5-$HT_6$ receptor antagonists [Foley A. G., Murphy K. J., Hirst W. D., Gallagher H. C., Hagan J. J., Upton N., Walsh F. S., Regan C. M. The 5-HT(6) receptor antagonist SB-271046 reverses scopolamine-disrupted consolidation of a passive avoidance task and ameliorates spatial task deficits in aged rats. *Neuropsychopharmacology.* 2004; 29: 93-100]. Recently more thorough understanding of 5-$HT_6$ receptor function in cognitive processes and more accurate conceptions concerning possible pharmacophoric properties of their antagonists were achieved. [Holenz J., Pauwels P. J., Diaz J. L., Merce R., Codony X., Buschmann H. Medicinal chemistry strategies to 5-$HT_6$ receptor ligands as potential cognitive enhancers and antiobesity agents. *Drug Disc. Today.* 2006; 11:283-299]. This resulted in preparation of highly affine selective ligands ("molecular tools"), and afterwards clinical candidates. At present a number of 5-$NT_6$ receptor antagonists are at various phases of clinical investigation as potential ingredients for treatment of AD, Huntington's disease, schizophrenia (antipsychotic) and other neurodegenerative and cognitive diseases (Table 1) [http://integrity.prous.com].

TABLE 1

5-$HT_6$ Receptor antagonists as drug candidates.

| Medicament | Clinical phase of testing | Developer | Therapeutic group |
|---|---|---|---|
| Dimebon ™ | Phase III | Medivation (USA) | Alzheimer's disease treatment |
| SGS-518 | Phase II | Lilly, Saegis | Cognitive diseases treatment |
| SB-742457 | Phase II | GlaxoSmithKline | Alzheimer's disease treatment; Antipsychotic |
| Dimebon* | Phase I/IIa | Medivation (USA) | Huntington's disease treatment |
| Dimebon* | Phase II | (Russia) | Schizophrenia |
| PRX-07034 | Phase I | Epix Pharm. | Obesity treatment; Antipsychotic; Cognitive diseases treatment |
| SB-737050A | Phase II | GlaxoSmithKline | Antipsychotic |
| BVT-74316 | Phase I | Biovitrum | Obesity treatment |
| SAM-315 | Phase I | Wyeth Pharm. | Alzheimer's disease treatment |
| SYN-114 | Phase I | Roche, Synosis Ther. | Cognitive diseases treatment |
| BGC-20-761 | Preclinical | BTG (London) | Antipsychotic; Cognitive diseases treatment |
| FMPO | Preclinical | Lilly | Antipsychotic |
| Dimebon ™ | Preclinical | (Russia) | Insult treatment |

Another attractive property of 5-$HT_6$ receptor antagonists is their ability to suppress appetite that can lead to preparation on their basis of essentially novel remedies for overweight lowering and obesity treatment. [Vicker S. P., Dourish C. T. Serotonin receptor ligands and the treatment of obesity. *Curr. Opin. Investig. Drugs.* 2004; 5:377-388]. This effect was confirmed in many investigations [Holenz J., Pauwels P. J., Diaz J. L., Merce R., Codony X., Buschmann H. Medicinal chemistry strategies to 5-HT$_6$ receptor ligands as potential cognitive enhancers and antiobesity agents. *Drug Disc. Today.* 2006; 11:283-299. Davies S. L. Drug discovery targets: 5-HT$_6$ receptor. *Drug Future.* 2005; 30:479-495]; its mechanism is based on suppression of γ-aminobutyric acid signaling by 5-HT$_6$ receptor antagonists and increasing of α-melanocyte-stimulating hormone emission, that, finally, results in lowering of food demand [Woolley M. L. 5-HT$_6$ receptors. *Curr. Drug Targets CNS Neurol. Disord.* 2004; 3:59-79]. Now two 5-HT$_6$ receptor antagonists are at the first phase of clinical testing as drug candidates for obesity treatment (Table 1) [http://integrity.prous.com].

In this context searching for new selective and effective serotonin 5-HT$_6$ receptor antagonists seems to be original and perspective approach to the development of novel drug substances for treating of a great number of neurological and neurodegenerative diseases and cognitive disorders.

There are many publications in scientific literature describing various biologically active arylsulfonyl substituted azaheterocycles, among them serotonin receptor ligands. For example, substituted 1-(2-aminoethyl)-4-(arylsulfonyl)pyrazoles of general formula A1 were described as serotonin 5-HT$_2$ receptor ligands [WO 2003057674 A1] and substituted 7-amino-3-(sulfonyl)pyrazolo[1,5-a]pyrimidines A2 as serotonin 5-HT$_6$ receptor antagonists [EP 941994 A1, 1999]

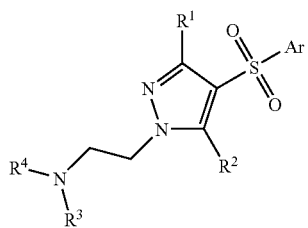

A1

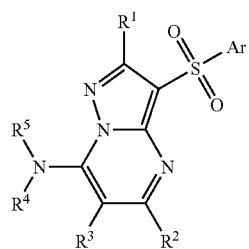

A2

A1: Ar=alkyl, aryl; R$^1$ and R$^2$=H, OH, alkyl, alkoxy; R$^3$ and R$^4$=H, alkyl, aryl.
A2: Ar=aryl, heterocyclyl; R$^1$=H, alkyl, alkylthio; R$^2$=H, alkyl, halogen; R$^3$=H, alkyl, hydroxyalkyl; R$^4$ and R$^5$=H; NR$^4$R$^5$=piperazinyl.

With the aim of working out novel highly effective neuroprotective medicaments the authors of the invention carried out widespread investigation in the field of substituted 3-(sulfonyl)pyrazolo[1,5-a]pyrimidines, as a result of which novel drug substances which were 5-HT$_6$ receptor antagonists have been found.

DISCLOSURE OF THE INVENTION

In the context of the present invention, the terms are generally defined as follows:
"Agonists" mean ligands being bound to receptors of definite type actively promote transferring their specific signal and by that cause biological response of the cell.

"Alkyl" means aliphatic hydrocarbon straight or branched group with 1-12 carbon atoms. Branched means alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k{}^aR_{k+1}{}^aN$—, $R_k{}^aR_{k+1}{}^aNC(=O)$—, $R_k{}^aR_{k+1}{}^aNC(=S)$—, $R_k{}^aR_{k+1}{}^aNSO_2$—, where $R_k{}^a$ and $R_{k+1}{}^a$ independently of each other represent "amino group" substituent, the meanings thereof are defined in this section, for example, hydrogen, alkyl, aryl, aralkyl, heteroaralkyl, heterocyclyl or heteroaryl, or $R_k{}^a$ and $R_{k+1}{}^a$ together with the N-atom, they are attached to, form through $R_k{}^a$ and $R_{k+1}{}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^aR_{k+1}{}^aN$—, $R_k{}^aR_{k+1}{}^aNC(=O)$—, annelated arylheterocyclenyl, annelated arylheterocyclyl.

"Alkoxy" means alkyl-O-group, wherein alkyl is defined in this section. The preferred alkoxy groups are methoxy, ethoxy, n-propoxy, iso-propoxy and n-butoxy.

"Amino group" means $R_k{}^aR_{k+1}{}^aN$-group substituted or not by "amino group substituent" $R_k{}^a$ and $R_{k+1}{}^a$, the meanings thereof are defined in this section, for example, amino (NH$_2$), methylamino, diethylamino, pyrrolidino, morpholino, benzylamino or phenethylamino.

"Annelated cycle" (condensed cycle) means bi- or poly-cyclic system wherein annelated cycle and cycle or polycycle with which it is annelated has, at least, two common atoms.

"Antagonists" mean ligands being bound to definite receptors do not cause active cellular responses. Antagonists prevent binding between agonists and receptors and by that block specific receptor signal transmission.

"Aryl" means aromatic mono- or polycyclic system with 6-14 carbon atoms, mainly from 6 to 10 C-atoms. Aryl may have one or more "cyclic system substituents" of the same or different structure. Phenyl, substituted phenyl, naphthyl, or substituted naphthyl are representatives of aryl groups. Aryl could be annelated with nonaromatic cyclic system or heterocycle.

"Arylsulfonyl" means aryl-SO$_2$-group, wherein the meaning of aryl is defined in this section.

"Heterocyclyl" means aromatic or nonaromatic monocyclic or polycyclic system comprising 3-10 carbon atoms, predominantly 5-6 carbon atoms, in which one or more carbon atoms are replaced by nitrogen, oxygen, or sulfur. The prefix "aza", "oxa" or "thia" before heterocyclyl means the occurrence in cyclic system nitrogen, oxygen or sulfur atoms, respectively. Heterocycyl may have one or more "cyclic system substituens" of the same or different structure. N- And S-atoms of heterocyclic fragment could be oxidized to N-oxide, S-oxide and S-dioxide. The representatives of heterocyclyl are: piperidinyl, pyrrolidinyl, piperazinyl, morpholinyl, thiomorpholinyl, thiazolidinyl, 1,4-dioxan-2-yl, tetrahydrofuranyl, tetrahydrothiophenyl and others.

"Hydrate" means stoichiometric or nonstoichiometric compositions of the compounds or their salts with water.

"Substituent" means chemical radical attached to scaffold (fragment), for example, "alkyl substituent", "amino group substituent", "carbamoyl substituent", and "cyclic system substituent", the meanings thereof are defined in this section.

"Amino group substituent" means substituent attached to amino group. Amino group substituent represents hydrogen, alkyl, cycloalkyl, aryl, heteroaryl, heterocyclyl, acyl, aroyl, alkylsulfonyl, arylsulfonyl, heteroarylsulfonyl, alkylaminocarbonyl, arylaminocarbonyl, heteroarylaminocarbonyl, heterocyclylaminocarbonyl, alkylaminothiocarbonyl, arylaminothiocarbonyl, heteroarylaminothiocarbonyl, heterocyclylaminothiocarbonyl, annelated heteroarylcycloalkenyl, annelated heteroarylcycloalkyl, annelated heteroarylheterocyclenyl, annelated hetcroarylheterocyclyl, annelated arylcycloalkenyl, annelated arylcycloalkyl, annelated arylheterocyclenyl, annelated arylheterocyclyli, alkoxycarbonylalkyl, aralkoxycarbonylalkyl, heteroaralkyloxycarbonylalkyl.

"Substituted amino group" means $R_k{}^a R_{k+1}{}^a$N-group wherein $R_k{}^a$ and $R_{k+1}{}^a$ represent amino group substituents the meanings thereof are defined in this section.

"Cognitive disorders" or disorders of cognitive functions" mean disorders (weakening) of mental abilities including attentiveness, memory, mentality, cognition, education, verbal, mental, executive and creative abilities, time and space orientation; in particular, cognitive disorders associated with AD, Parkinson's and Huntington's diseases, senile dementia; age-associated memory impairment, AAMI; dysmetabolic encephalopathy; psychogenous memory impairment; amnesia; amnesic disturbances; transit global amnesia; dissociative amnesia; vascular dementia; light or mild cognitive impairment (MCI); attention deficit hyperactivity disorder (AD/HD); cognitive impairments, accompanying psychotic diseases, epilepsy, delirium, autism, psychosis, Down's syndrome, bipolar disorders and depression; AIDS-associated dementia; dementias at hypothyroidism; dementia connected with alcohol, substances causing dependability and neurotoxins; dementia accompanying neurodegenerative diseases, for example, cerebellar degeneracy and amyotrophic lateral sclerosis; cognitive disturbances connected with cerebral crisis, infectious and oncological brain diseases as well as traumatic brain injury; cognitive function damages associated with autoimmune and endocrine diseases, and others.

"Drug substance" means physiologically active compound of synthetic or other (biotechnological, vegetable, animal, microbe and so on) origin exhibiting pharmacological activity and being an active ingredient of pharmaceutical composition employed in production and preparation of medicaments.

"Medicament"—is compound or mixture of compounds representing pharmaceutical composition in the form of tablets, capsules, injections, ointments and other finished pharma products intended for restoration, improvement or modification of physiological functions at humans and animals, and for treatment and prophylaxis of diseases, diagnostics, anesthesia, contraception, cosmetology and others.

"Ligands" (from Latin ligo) represent chemical compounds (small molecule, peptide, protein, inorganic ion, and others) capable to interact with receptors which convert this interaction into specific signal.

"Neurodegenerative diseases" means specific conditions and diseases, accompanied by damage and primary destruction of nervous cell populations in the certain areas of central nervous system. Neurodegenerative diseases include but are not limited by: AD; Parkinson's and Huntington's diseases (chorea); multiocular sclerosis; cerebellar degeneracy; amyotrophic lateral sclerosis; dementias with Lewy bodies; spinal muscular atrophy; peripherical neuropathy; spongy encephalitis (Creutzfeld-Jakob Disease); AIDS dementia; multi-infract dementia; frontotemporal dementias; leukoencephalopathy (spongy degeneration of white matter); chronic neurodegenerative diseases; cerebral crisis; ischemic, reperfusion and hypoxic brain damage; epilepsy; cerebral ischemia; glaucoma; traumatic brain injury; Down's syndrome; encephalomyelitis; meningitis; encephalitis; neuroblastoma; schizophrenia; depression. Moreover, neurodegenerative diseases include pathological states and disorders associated with hypoxia, substance abuse, causing dependability under neurotoxins influence; infectious and oncological brain diseases as well as neuronal damages associated with autoimmune and endocrine diseases and others.

"Substituted sulfonyl" means $R-SO_2$-group wherein R could be selected from alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, the meanings thereof are defined in this section.

"Receptors" (from Latin recipere) represent biological macromolecules located either on cytoplasmic cell membrane or intracellular, capable specifically interact with restricted number of physiologically active compounds (ligands) and transform the signal of this interaction into definite cellular response.

"Therapeutic kit" is simultaneously administered combination of two or more drug substances with different mechanism of pharmacological action and aimed at different biotargets taking part in pathogenesis of the disease.

"Pharmaceutical composition" means composition comprising, at least, one of compounds of general formula 1 and, at least, one of components selected from pharmaceutically acceptable and pharmacologically compatible fillers, solvents, diluents, auxiliary, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dosage. Examples of suitable suspending agents are: ethoxylated isostearyl alcohol, polyoxyethene, sorbitol and sorbitol ether, microcrystalline cellulose, aluminum metahydroxide, bentonite, agar-agar and tragacant and mixtures thereof as well. Protection against microorganism action can be provided by various antibacterial and antifungal agents, such as: parabens, chlorobutanol, sorbic acid, and similar compounds. Composition may also contain isotonic agents, such as: sugar, sodium chloride, and similar compounds. Prolonged effect of the composition may be achieved by agents slowing down absorption of the active ingredient, for example, aluminum monostearate and gelatin. Examples of suitable carriers, solvents, diluents and delivery agents include water, ethanol, polyalcohols and their mixtures, natural oils (such as olive oil) and injection-grade organic esters (such as ethyl oleate). Examples of fillers are: lactose, milk-sugar, sodium citrate, calcium carbonate, calcium phosphate and the like. Examples of disintegrators and distributors are: starch, alginic acid and its salts, and silicates. Examples of suitable lubricants are: magnesium stearate, sodium lauryl sulfate, talc and polyethylene glycol of high molecular weight. Pharmaceutical composition for peroral, sublingual, transdermal, intramuscular, intravenous, subcutaneous, local or rectal administration of active ingredient, alone or in combination with another active compound may be administered to humans and animals in standard administration form, or in mixture with traditional pharmaceutical carriers. Suitable standard administration forms include peroral forms such as tablets, gelatin capsules, pills, powders, granules, chewing-gums and peroral solutions or suspensions, for example, therapeutic kit; sublingual and transbuccal administration forms; aerosols; implants; local, transdermal, subcutaneous, intramuscular, intravenous, intranasal or intraocular forms and rectal administration forms. "Pharmaceutically acceptable salt" means relatively nontoxic both organic and inorganic salts of acids and bases disclosed in this invention. Salts could be prepared in situ in processes of synthesis, isolation or purification of compounds or they could be prepared specially. In particular, salts of bases could be prepared starting from purified bases disclosed in the invention and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of such salt properties is given in: Berge S. M., et al., "Pharmaceutical Salts" J. Pharm. Sci., 1977, 66: 1-19). Salts of disclosed acids may be prepared by reaction of purified acids specifically with suitable base; moreover, metal salts and amine salts may be synthesized too. Metal salts are salts of sodium, potassium, calcium, barium, magnesium, lithium and aluminum; sodium and potassium salts being preferred. Suitable inorganic bases from which metal salts can be prepared are: sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of disclosed acid salts are amines and amino acids the basicity of which is sufficient enough to produce stable salt and suitable for use in medical purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as holine, tetramethylammonium, tetraethylammonium, and the like. Amino acids may be selected from the main aminoacids-lysine, ornithine and arginine.

The subject of the present invention is novel substituted 2-amino-3-(sulfonyl)pyrazolo[1,5-a]pyrimidines of general formula 1 and pharmaceutically acceptable salts and/or hydrates thereof,

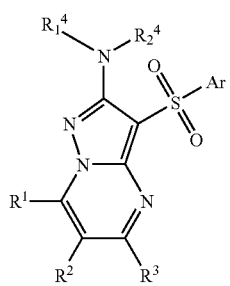

wherein:

Ar represents optionally substituted aryl or optionally substituted heterocyclyl;

$R^1$ and $R^3$ independently of each other represent $C_1$-$C_3$ alkyl or phenyl;

$R^2$ represents hydrogen or $C_1$-$C_3$ alkyl;

$R^4_1$, $R^4_2$ independently of each other represent hydrogen, optionally substituted $C_1$-$C_3$ alkyl or optionally substituted phenyl, or $R^4_1$, and $R^4_2$ together with the nitrogen atom they are attached to form optionally substituted heterocyclyl.

The preferred substituted 2-amino-3-(sulfonyl)pyrazolo[1,5-a]pyrimidines are substituted 5,7-dimethyl-3-(arylsulfonyl)pyrazolo[1,5-a]pyrimidines of general formula 1.1 or pharmaceutically acceptable salts and/or hydrates thereof,

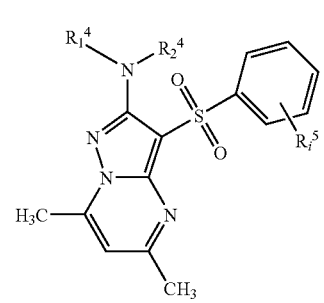

wherein:

$R^4_1$, and $R^4_2$ are all as mentioned above; $R_i^5$ represents one or two optionally identical substituents selected from hydrogen, lower alkyl, trifluoromethyl or halogen.

The preferable compounds of general formula 1.1 are: 2-methylamino-5,7-dimethyl-3-(phenylsulfonyl)pyrazolo[1,5-a]pyrimidine 1.1(1), 2-dimethylamino-5,7-dimethyl-3-(phenylsulfonyl)pyrazolo[1,5-a]pyrimidine 1.1(2), 2-methylamino-5,7-dimethyl-3-(4-fluorophenylsulfonyl)pyrazolo[1,5-a]pyrimidine 1.1(3), 2-dimethylamino-5,7-dimethyl-3-(4-fluorophenylsulfonyl)pyrazolo[1,5-a]pyrimidine 1.1(4), 2-methylamino-5,7-dimethyl-3-(3-fluorophenylsulfonyl)pyrazolo[1,5-a]pyrimidine 1.1(5), 2-dimethylamino-5,7-dimethyl-3-(3-fluorophenylsulfonyl)pyrazolo[1,5-a]pyrimidine 1.1(6), 2-methylamino-5,7-dimethyl-3-(3-chlorophenylsulfonyl)pyrazolo[1,5-a]pyrimidine 1.1(7), 2-dimethylamino-5,7-dimethyl-3-(3-chlorophenylsulfonyl) pyrazolo[1,5-a]pyrimidine 1.1(8) or pharmaceutically acceptable salts and/or hydrates thereof,

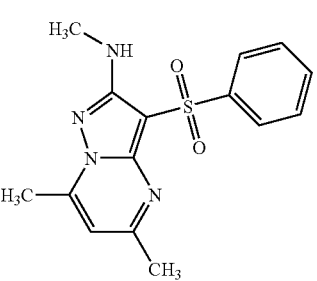

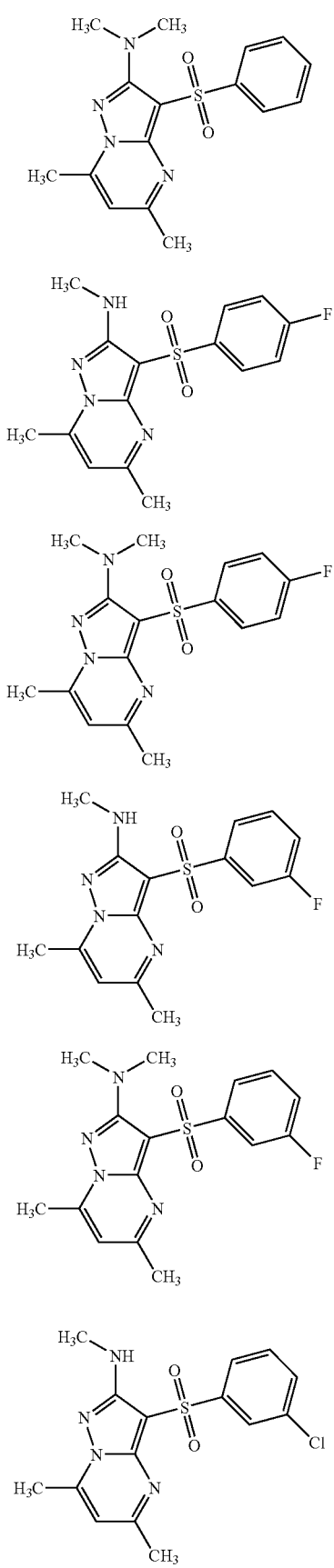

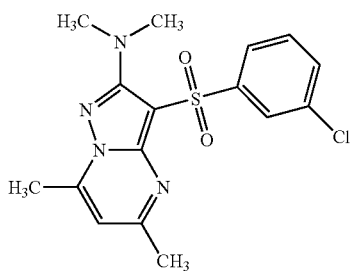

The subject of the present invention is also method for preparation of novel substituted 2-amino-3-(sulfonyl)pyrazolo[1,5-a]pyrimidines of general formula 1 by interaction of substituted 3-amino-4-(sulfonyl)-2H-pyrazoles of general formula 2 with β-diketones of general formula 3 and subsequent isolation or separation of the reaction products (1A, 1B) according to scheme given below.

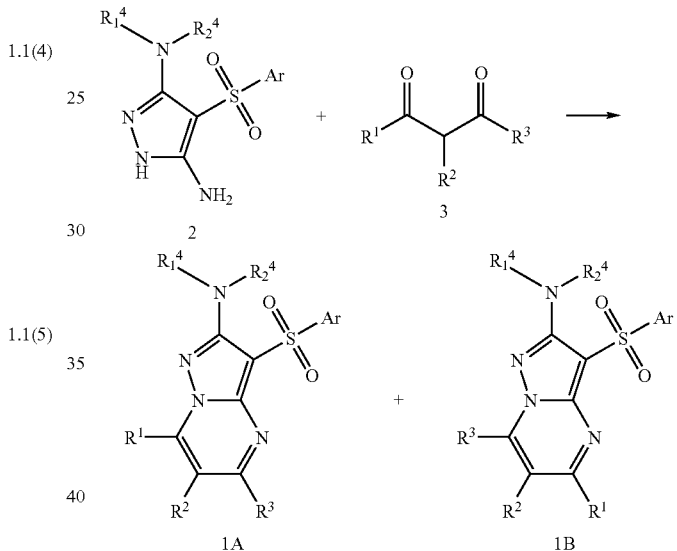

wherein: Ar, $R^1$, $R^2$, $R^3$, $R^4_1$, and $R^4_2$ are all as mentioned above.

If diketones 3 are symmetrical compounds ($R^1=R^3$), only one product of the reaction could be obtained. If diketones used are unsymmetrical ($R^1 \neq R^3$), mixture of two isomeric products of the reaction 1A and 1B are usually formed, which could be separated by well known methods, for example, recrystallization or preparative chromatography.

The subject of the present invention is the development of novel serotonin 5-$HT_6$ receptor antagonists and novel biologically active substances.

The subject in view is achieved by serotonin 5-$HT_6$ receptor antagonists, which are substituted 2-amino-3-(sulfonyl) pyrazolo[1,5-a]pyrimidines of general formulas 1, 1.1, 1.1 (1), 1.1(2), 1.1(3), 1.1(4), 1.1(5), 1.1(6), 1.1(7), 1.1(8) or pharmaceutically acceptable salts and/or hydrates thereof.

The subject of the present invention is a drug substance for pharmaceutical compositions and medicaments which is, at least, one of substituted 2-amino-3-(sulfonyl)pyrazolo[1,5-a] pyrimidines of general formulas 1, 1.1, 1.1(1), 1.1(2), 1.1(3), 1.1(4), 1.1(5), 1.1(6), 1.1(7), 1.1(8) or pharmaceutically acceptable salts and/or hydrates thereof.

The subject of the present invention is also a pharmaceutical composition interacting with serotonin 5-$HT_6$ receptors for prophylaxis and treatment of various conditions and diseases of CNS of humans and warm blooded animals comprising pharmaceutically effective amount of novel drug substance which is, at least, one of 2-amino-3-(sulfonyl)pyrazolo[1,5-a]pyrimidines of general formulas 1, 1.1, 1.1(1), 1.1(2), 1.1(3), 1.1(4), 1.1(5), 1.1(6), 1.1(7), 1.1(8) or pharmaceutically acceptable salts and/or hydrates thereof.

Pharmaceutical compositions may include pharmaceutically acceptable excipients. Pharmaceutically acceptable excipients mean diluents, auxiliary agents and/or carriers applied in the sphere of pharmaceutics. According to the invention pharmaceutical composition together with a drug substance of general formula 1 may contain other active ingredients provided that they do not give rise to undesirable effects, for example, allergic reactions.

If needed, according to the present invention pharmaceutical compositions can be used in clinical practice in various forms prepared by mixing the said compositions with traditional pharmaceutical carries; for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

According to the present invention the carriers used in pharmaceutical compositions represent carriers which are used in the sphere of pharmaceutics for preparation of commonly applied forms. Binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The subject of the present invention is also method for preparation of pharmaceutical composition by mixing drug substance which is, at least, one of substituted 2-amino-3-(sulfonyl)pyrazolo[1,5-a]pyrimidines of general formulas 1, 1.1, or compounds of formulas 1.1(1), 1.1(2), 1.1(3), 1.1(4), 1.1(5), 1.1(6), 1.1(7), 1.1(8) or pharmaceutically acceptable salts and/or hydrates thereof with inert exicipient and/or solvent.

The subject of the present invention is also a medicament in the form of tablets, capsules, or injections, placed in pharmaceutically acceptable packing intended for treatment and prophylaxis of CNS diseases pathogenesis of which is associated with the disturbance of serotonin 5-$HT_6$ receptor activation, comprising drug substance which is, at least, one of substituted 2-amino-3-(sulfonyl)pyrazolo[1,5-a]pyrimidines of general formulas 1, 1.1, 1.1(1), 1.1(2), 1.1(3), 1.1(4), 1.1(5), 1.1(6), 1.1(7), 1.1(8) or pharmaceutically acceptable salts and/or hydrates thereof, or pharmaceutical composition comprising this drug substance.

According to the present invention the preferable medicament is a medicament intended for prophylaxis and treatment of Alzheimer's disease and Huntington's disease.

According to the invention the preferable medicament is a medicament intended for prophylaxis and treatment of psychic disorders and schizophrenia.

According to the invention the preferable medicament is a medicament intended for prophylaxis and treatment of obesity.

The subject of the present invention is also therapeutic kit for prophylaxis and treatment of various diseases pathogenesis of which is associated with serotonin 5-$HT_6$ receptors at humans and animals comprising novel medicament or drug substance of general formulas 1.1, 1.1, 1.1(1), 1.1(2), 1.1(3), 1.1(4), 1.1(5), 1.1(6), 1.1(7), 1.1(8) or pharmaceutical composition including this drug substance.

According to the present invention the preferable therapeutic kit is a therapeutic kit for prophylaxis and treatment of neurologic disorders, neurodegenerative and cognitive diseases at humans and animals comprising novel medicament or drug substance of general formulas 1.1, 1.1(1), 1.1(2), 1.1(3), 1.1(4), 1.1(5), 1.1(6), 1.1(7), 1.1(8) or pharmaceutical composition including this drug substance.

According to the present invention the preferable therapeutic kit is a therapeutic kit for prophylaxis and treatment of AD, Huntington's disease, psychic disorders, schizophrenia, hypoxia-ischemia, hypoglycemia, convulsive states, brain injuries, lathyrism, amyotrophic lateral sclerosis, obesity or insult, comprising novel medicament or drug substance of general formulas 1, 1.1, 1.1(1), 1.1(2), 1.1(3), 1.1(4), 1.1(5), 1.1(6), 1.1(7), 1.1(8), or pharmaceutical composition including this drug substance.

The therapeutic kit for prophylaxis and treatment of various diseases, pathogenesis of which is associated with serotonin 5-$HT_6$ receptors at humans and animals, among them neurological disorders, neurodegenerative and cognitive diseases, for prophylaxis and treatment of AD, Huntington's disease, psychotic disorders and schizophrenia, hypoxia-ischemia, hypoglycemia, convulsive states, brain injuries, lathyrism, amyotrophic lateral sclerosis, and insult, along with drug substances disclosed in the invention, may include other active ingredients such as: nonsteroidal anti-inflammatory drugs (Orthophene, Indomethacin, Ibuprophen and others); acetyl cholinesterase inhibitors (Tacrine, Amiridine, Fizostigmine, Aricept, Phenserine and others); estrogens (for example, Estradiol); NMDA-receptor antagonists (for example, Memantine, Neramexane); nootropic drugs (for example, Pyracetam, Fenibut and others); AMPA receptor modulators (for example, Ampalex); antagonists of cannabinoid receptors CB-1 (for example, Rimonabant); monoaminooxidase inhibitors MAO-B and/or MAO-A (for example, Rasagiline); antiamyloidogenic drugs (for example, Tramiprosate); lowering β-amyloide neurotoxicity compounds (for example, Indole-3-propionic acid); γ- and/or β-secretase inhibitors; M1-muscarinic receptor agonists (for example, Cevimeline); metal helates (for example, Clioquinol); GABA (A) receptor antagonists (for example, CGP-36742); monoclonal antibodies (for example, Bapineuzumab); antioxidants; neurotrophic agents (for example, Cerebrolisine); antidepressants (for example, Imipramine, Sertraline and others) and others.

According to the present invention the preferable therapeutic kit is a therapeutic kit for overweight lowering and obesity treatment. The therapeutic kit for overweight lowering and obesity treatment along with drug substances disclosed in the invention, may include other active ingredients such as: anorectic drugs (for example, Fepranon, Desopimon, Masindole); hormone drugs (for example, Tireoidine); hypolipidemic means such as fibrates (for example, Fenofibrate); statines (for example, Lovastatine, Simvastatine, Pravastatine and Probucol); hypoglycemic drugs (sulfonylureas—for example, Butamide, Glibenclamide; biguanidines—for example, Buformine, Metamorphine) and drugs with some other mechanism of action, such as cannabinoid CB-1 receptor antagonists (Rimonabant), inhibitors of norepinephrine and serotonin reuptake (Sibutramine), inhibitors of ferments of fatty acids synthesis (Orlistat) and others, along with antioxidants, food additives and others.

The subject of the present invention is also method for prophylaxis and treatment of various diseases of CNS pathogenesis of which is associated with serotonin 5-$HT_6$ receptors at humans and animals, among them neurological disorders, neurodegenerative and cognitive diseases, by introduction of novel drug substance, or pharmaceutical composition, or medicament, or therapeutic kit to the said mammals.

Medicaments could be introduced peroral or parenterally (for example, intravenously, subcutaneously, intraperitoneally or locally). The clinical dose of pharmaceutical composition or medicament comprising drug substance of general formulas 1, 1.1, 1.1(1), 1.1(2), 1.1(3), 1.1(4), 1.1(5), 1.1(6), 1.1(7), 1.1(8) may be corrected depending on: therapeutic efficiency and bio-accessibility of active ingredients in patients' organism, rate of their exchange and removal from organism, and age, gender, and severity of patient's symptoms. Thus, the daily intake for adults normally being 10~500 mg, preferably 50~300 mg. Accordingly, the above effective doses are to be taken into consideration while preparing medicament of the present invention, each dose unit of the medicament contains 10~500 mg of compound of general formulas 1, 1.1, 1.1(1), 1.1(2), 1.1(3), 1.1(4), 1.1(5), 1.1(6), 1.1(7), 1.1(8), preferably 50~300 mg. Following the instructions of physician or pharmacist, the medicaments may be taken several times over specified periods of time (preferably, from one to six times).

BEST EMBODIMENT OF THE INVENTION

The invention is illustrated by the following FIGURE

FIG. 1. Concentration dependence of serotonin 5-$HT_6$ receptor and Methiothepin (control) inhibition by drug substance 1.1(1).

Below the invention is described by means of specific examples, which illustrate but not limit the scope of the invention.

EXAMPLE 1

General method for preparation of substituted 2-amino-3-(sulfonyl)pyrazolo[1,5-a]pyrimidines of general formulas 1, 1.1. Mixture of 0.005 mol of substituted 3,4-diamino-pyrazole 2 and 0.0055 mol of corresponding diketone 3 in 5 ml of acetic acid was boiled for 4 hours. After cooling the solid precipitated was filtered off, washed with methanol and water. If necessary, the product was subjected to recrystallization from proper solvent, or chromatographic purification or chromatographic separation. Yield of 3-(sulfonyl)pyrazolo[1,5-a]pyrimidines of general formulas 1, 1.1 was 70%-85%. Some of novel substituted 2-amino-3-(sulfonyl)pyrazolo[1,5-a]pyrimidines of general formulas 1, 1.1, 1.1(1), 1.1(2), 1.1(3), 1.1(4), 1.1(5), 1.1(6), 1.1(7), 1.1(8), their LCMS and NMR data, and % inhibition of 5-$HT_6$ receptors are presented in Table 2.

TABLE 2

| 2-Amino-3-(sulfonyl)pyrazolo[1,5-a]pyrimidines of general formulas 1, 1.1. | | | | | |
|---|---|---|---|---|---|
| No | Formula | Mol.w. | LCMS, m/z (M + 1) | $^1$H NMR, DMSO-d6, δ, ppm: | % * |
| 1(1) | | 406.51 | 407 | | 77 |
| 1(2) | | 378.46 | 379 | | 90 |
| 1(3) | | 378.46 | 379 | | 91 |

TABLE 2-continued

2-Amino-3-(sulfonyl)pyrazolo[1,5-a]pyrimidines of general formulas 1, 1.1.

| No | Formula | Mol.w. | LCMS, m/z (M + 1) | $^1$H NMR, DMSO-d6, δ, ppm: | % * |
|---|---|---|---|---|---|
| 1(4) | | 317.37 | 318 | | 97 |
| 1(5) | | 317.37 | 318 | | 95 |
| 1(6) | | 322.41 | 323 | | 98 |
| 1(7) | | 330.41 | 331 | | 104 |
| 1(8) | | 409.94 | 374 | $^1$H NMR (DMSO)-D$_6$) 10.07 (br.s, 1H); 8.02 (d, J = 8.0 Hz, 2H); 7.52-7.62 (m, 3H); 6.95 (s, 1H); 6.72 (br.m, J = 5.7 Hz, 1H); 3.69-3.76 (m, 2H); 3.29-3.35 (m, 2H); 2.80 (s, 6H); 2.54 (s, 3H); 2.47 (s, 3H). | 91 |

TABLE 2-continued

2-Amino-3-(sulfonyl)pyrazolo[1,5-a]pyrimidines of general formulas 1, 1.1.

| No | Formula | Mol.w. | LCMS, m/z (M + 1) | ¹H NMR, DMSO-d6, δ, ppm: | % * |
|---|---|---|---|---|---|
| 1(9) | | 423.97 | 388 | ¹H NMR (DMSO)-$D_6$) 10.46 (br.s, 1H); 8.01 (d, J = 8.0 Hz, 2H); 7.52-7.62 (m, 3H); 7.04 (s, 1H); 3.73 (t, J = 6.6 Hz, 2H); 3.36 (t, J = 6.6 Hz, 2H); 3.03 (s, 3H); 2.78 (s, 6H); 2.58 (s, 3H); 2.48 (s, 3H). | 88 |
| 1(10) | | 423.97 | 388 | ¹H NMR (DMSO)-$D_6$) 10.30 (br.s, 1H); 8.01 (d, J = 8.0 Hz, 2H); 7.52-7.62 (m, 3H); 6.92 (s, 1H); 6.52 (br.t, J = 6.1 Hz, 1H); 3.38-3.44 (m, 2H); 3.02-3.08 (m, 2H); 2.72 (s, 6H); 2.52 (s, 3H); 2.46 (s, 3H); 1.92-2.06 (m, 2H). | 94 |
| 1(11) | | 471.58 | 472 | ¹H NMR (CDCl₃) 8.14 (d, J = 7.7 Hz, 2H); 7.42-7.54 (m, 3H); 6.64 (s, 1H); 3.59-3.65 (m, 4H); 3.43-3.49 (m, 4H); 2.63 (s, 3H); 2.58 (s, 3H); 1.49 (s, 9H). | 63 |

TABLE 2-continued
2-Amino-3-(sulfonyl)pyrazolo[1,5-a]pyrimidines of general formulas 1, 1.1.
| No | Formula | Mol.w. | LCMS, m/z (M + 1) | $^1$H NMR, DMSO-d6, δ, ppm: | % * |
|---|---|---|---|---|---|
| 1(12) | 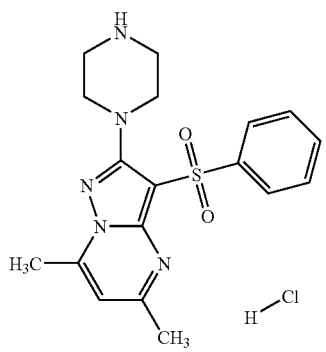 | 407.92 | 372 | $^1$H NMR (DMSO)-D$_6$) 9.57 (br.s, 2H); 8.01 (d, J = 8.0 Hz, 2H); 7.49-7.62 (m, 3H); 7.06 (s, 1H); 3.57-3.65 (m, 4H); 3.16-3.26 (m, 4H); 2.57 (s, 3H); 2.50 (s, 3H). | 76 |
| 1(13) | 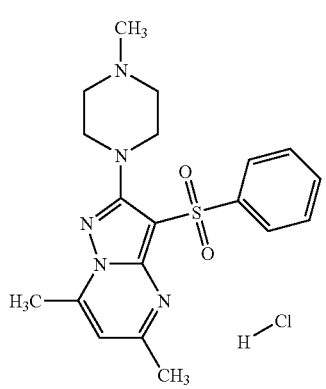 | 421.95 | 386 | | 80 |
| 1(14) | 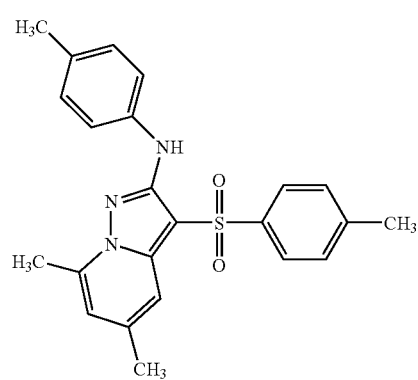 | 406.51 | 407 | | 70 |
| 1.1(1) | 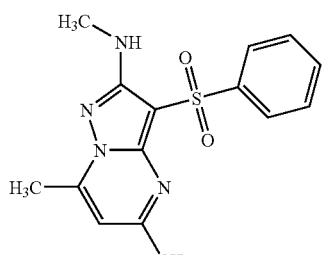 | 316.38 | 317 | $^1$H NMR (DMSO)-D$_6$, 400 MHz) δ 8.01-8.04 (m, 2H), 7.53-7.62 (m, 3H), 6.90 (s, 1H), 6.34 (q, J = 4.4 Hz, 1H), 2.91 (d, J = 4.4 Hz, 3H), 2.54 (s, 3H), 2.48 (s, 3H). $^1$H NMR-(CDCl$_3$): 8.14 (d, J = 8.5 Hz, 2H); 7.40-7.51 (m, 3H); 6.51 (s, 1H); 5.99 (br. q, J = 5.1 Hz, 1H); 3.02 (d, J = 5.1 Hz, 3H); 2.57 (s, 3H); 2.53 (s, 3H). $^{13}$C NMR- (CDCl$_3$): 161.2; 160.3; 158.2 147.8; 145.2; 144.0; 132.3; 128.6; 128.4; 109.1; 29.0; 24.8; 17.0. | 77 |

TABLE 2-continued
2-Amino-3-(sulfonyl)pyrazolo[1,5-a]pyrimidines of general formulas 1, 1.1.
| No | Formula | Mol.w. | LCMS, m/z (M + 1) | ¹H NMR, DMSO-d6, δ, ppm: | % * |
|---|---|---|---|---|---|
| 1.1(2) | 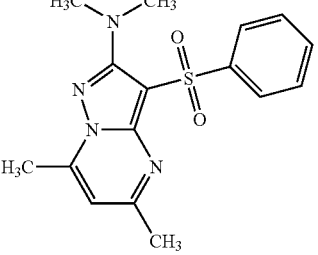 | 330.41 | 331 | | 86 |
| 1.1(3) | 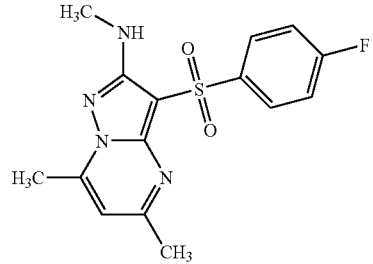 | 334.37 | 335 | ¹H PMR (CDCl₃), 400 MHz): δ 8.18 (m, 2H), 7.13 (m, 2H), 6.56 (s, 1H), 5.99 (q, J = 4.8 Hz, 1H), 3.05 (d, J = 4.8 Hz, 3H), 2.61 (s, 1H), 2.56 (s, 1H). | 99 |
| 1.1(4) | 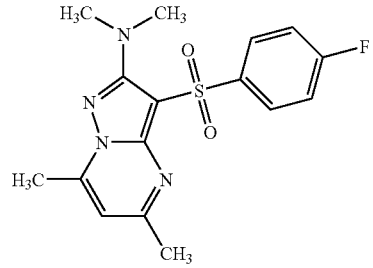 | 348.40 | 349 | | 95 |
| 1.1(5) | 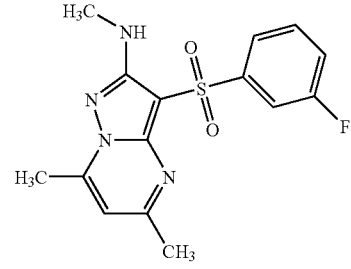 | 334.37 | 335 | | 97 |
| 1.1(6) | 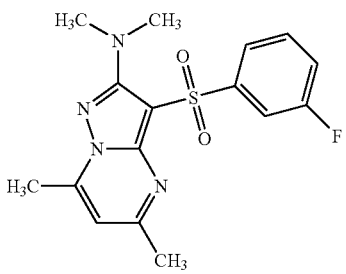 | 334.37 | 335 | | 97 |

TABLE 2-continued

2-Amino-3-(sulfonyl)pyrazolo[1,5-a]pyrimidines of general formulas 1, 1.1.

| No | Formula | Mol.w. | LCMS, m/z (M + 1) | $^1$H NMR, DMSO-d6, δ, ppm: | % * |
|---|---|---|---|---|---|
| 1.1(7) | | 350.83 | 351 | $^1$H NMR (DMSO)-D$_6$, 400 MHz): δ 8.22 (s, 1H), 8.04 (d, J = 7.6 Hz, 1H), 7.44 (m, 1H), 7.40 (t, J = 7.6 Hz, 1H), 6.57 (s, 1H), 5.97 (q, J = 5.2 Hz, 1H), 3.05 (d, J = 5.2 Hz, 3H), 2.61 (s, 3H), 2.58 (s, 3H). | 100 |
| 1.1(8) | | 364.86 | 365 | | 96 |
| 1.1(9) | | 368.82 | 369 | $^1$H NMR (CDCl$_3$, 400 MHz): δ 8.32 (dd, J$_1$ = 6.8 Hz, J$_2$ = 2.4 Hz, 1H), 8.11 (dd, J$_1$ = 6.8 Hz, J$_2$ = 4.4 Hz, J$_3$ = 2.4 Hz, 1H), 7.21 (t, J = 8.8 Hz, 1H), 6.58 (s, 1H), 5.95 (q, J = 5.2 Hz, 1H), 3.05 (d, J = 5.2 Hz, 3H), 2.62 (s, 3H), 2.57 (s, 3H). | 97 |

* % inhibition of 5-HT$_6$ receptors by 10 μM solutions of substituted 2-amino-3-(sulfonyl)pyrazolo[1,5-a]pyrimidines of general formulas 1, 1.1.

EXAMPLE 2

Determination of antagonistic activity of compounds of general formula 1 towards 5-HT$_6$ receptors. Compounds of general formula 1 were tested for their ability to prevent 5-HT$_6$ receptor activation by serotonin. HEK 293 cells (cells of human embryo's kidney) with artificially expressed 5-HT$_6$ receptor, activation of which by serotonin leads to increasing the concentration of intracellular cAMP were used. The content of intracellular cAMP was determined using reagent kit LANCE cAMP (PerkinElmer) according to the method described by the manufacturer of the kit [http://las.perkinelmer.com/content/Manuals/MAN_LANCEcAMP384KitUser.pdf].

Effectiveness of compounds was estimated by their ability to reduce the content of intracellular cAMP induced by serotonin.

Table 3 presents data on % inhibition of 5-HT$_6$ receptors by 10 μM solutions of compounds of general formula 1. As can be seen from the data given, tested compounds show observable activity towards serotonin 5-HT$_6$ receptors.

Table 3 shows values of IC$_{50}$ inhibition of intracellular cAMP production stimulated by serotonin by some compounds of general formula 1, testifying antagonistic activity thereof in the setting of functional assay.

TABLE 3

IC$_{50}$ inhibition of serotonin 5-HT$_6$ receptors by compounds of general formula 1 in the setting of functional assay.

| No substance | IC$_{50}$, nM |
|---|---|
| 1.1(1) | 5.0 |
| 1.1(2) | 1177 |
| 1.1(3) | 6.0 |
| 1.1(5) | 5.0 |
| 1.1(7) | 2.0 |
| 1.1(9) | 4.0 |

EXAMPLE 3

Activity determination of serotonin 5-HT$_6$ receptor antagonists of the general formula 1 in the setting of competitive binding to serotonin 5-HT$_6$ receptors.

Screening of the disclosed compounds for their potential ability to interact with serotonin 5-HT$_6$ receptors was carried out by method of radioligand binding. For this purpose membrane species were prepared from expressing recombinant human 5-HT$_6$ receptors HeLa cells by means of their homogenization in glass homogenizer with subsequent separation of plasmatic membranes from cell nuclei, mitochondria's and cell wreckages by differential centrifugation. Determination of tested compounds binding with 5-HT$_6$ receptors was carried out according to the method described in [Monsma F J Jr, Shen Y, Ward R P, Hamblin M W and Sibley D R, Cloning and expression of a novel serotonin receptor with high affinity for tricyclic psychotropic drugs. Mol Pharmacol. 43: 320-327, 1993]. In the preferable embodiment membrane preparations were incubated with radioligand (1.5 nM [$^3$H] Lysergic acid diethylamide) without and in the presence of investigated compounds for 120 min at 37° C. in medium consisting of mM Tris-HCl, pH 7.4, 150 mM NaCl, 2 mM Ascorbic Acid, 0.001% BSA. After incubation the samples were filtered in vacuo on glass-microfiber filters G/F (Millipor, USA), filters were washed three times with cold solution of medium and radioactivity was measured by scintillation counter Micro-Beta 340 (PerkinElmer, USA). Nonspecific binding which made up 30% of overall binding was determined by incubation of membrane preparations with radioligand in the presence of 5 µM Serotonin (5-HT). Methiothepin was used as positive control. Binding of tested compounds to the receptor was determined by their ability to displace the radioligand and expressed in percent of displacement. The percent of displacement was calculated according to the following equation:

$$\% \ I = \frac{TA - CA}{TA - NA} * 100,$$

wherein: TA—was overall radioactivity in the presence of radioligand only, CA—was radioactivity in the presence of radioligand and tested compound and NA—was radioactivity in the presence of radioligand and Serotonin (5 µM).

Table 4 and FIG. 1 present, as one of the examples, the test results for 5,7-dimethyl-2-methylamino-3-(phenylsulfonyl)pyrazolo[1,5-a]pyrimidine 1.1(1) and Methiothepin (control compound), which testify the high activity (4.61 nM) of this serotonin 5-HT$_6$ receptor antagonist.

TABLE 4

Concentration dependence of serotonin 5-HT$_6$ receptor inhibition by drug substance of formula 1.1(1) and IC$_{50}$ and K$_i$ values in the setting of competitive binding.

| Compound | Concentration dependences | IC$_{50}$, nM | K$_i$, nM |
|---|---|---|---|
| ● Substance 1.1(1) | FIG. 1. | 0.511 | 0.237 |
| ■ Control-Methiothepin | | 1.3 | 0.603 |

EXAMPLE 4

Medicament preparation in the form of tablets. 1600 mg Of starch, 1600 mg of ground lactose, 400 mg of talk and 1000 mg of 5,7-dimethyl-2-methylamino-3-(phenylsulfonyl)pyrazolo[1,5-a]pyrimidine 1.1(1) were mixed together and pressed into bar. The resultant bar was comminuted into granules and sifted through sieve to collect granules of 14-16 mesh. The granules thus obtained were shaped into tablets of suitable form weighing 560 mg each.

EXAMPLE 5

Medicament preparation in the form of capsules. 5,7-Dimethyl-2-methylamino-3-(phenylsulfonyl)pyrazolo[1,5-a]pyrimidine 1.1(1) and lactose powder were carefully mixed in ratio 2:1. The resultant powdery mixture was packed into gelatin capsules of suitable size by 300 mg to capsule.

EXAMPLE 6

Medicament preparation of in the form of compositions for intramuscular, intraperitoneal or hypodermic injections. 500 mg of 5,7-dimethyl-2-methylamino-3-(phenylsulfonyl)pyrazolo[1,5-a]pyrimidine 1.1(1), 300 mg of chlorobutanol, 2 ml of propylene glycol, and 100 ml of injectable water were mixed together. The resultant solution was filtered and placed into 1 ml ampoules, which were sealed and sterilized in autoclave.

INDUSTRIAL APPLICABILITY

The invention could be used in medicine, veterinary, biochemistry.

The invention claimed is:
1. A substituted 2-amino-3-(sulfonyl)pyrazolo[1,5-a]pyrimidine compound of general formula 1, or pharmaceutically acceptable salt thereof,

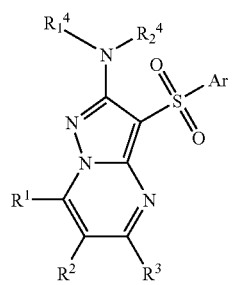

wherein:
Ar is aryl selected from optionally substituted phenyl or optionally substituted 5-6-membered heteroaryl, containing as the heteroatom nitrogen or sulfur atom;
R$^1$ and R$^3$ independently of each other represent C$_1$-C$_3$ alkyl or phenyl;
R$^2$ represents hydrogen or C$_1$-C$_3$ alkyl;
R$^4_1$, R$^4_2$ independently of each other represent hydrogen, optionally substituted C$_1$-C$_3$ alkyl or optionally substituted phenyl, or R$^4_1$ and R$^4_2$ together with the nitrogen atom they are attached to form optionally substituted heterocyclyl.
2. The compound of claim 1, representing substituted 5,7-dimethyl-3-(arylsulfonyl)pyrazolo[1,5-a]pyrimidine of general formula 1.1, or pharmaceutically acceptable salt thereof,

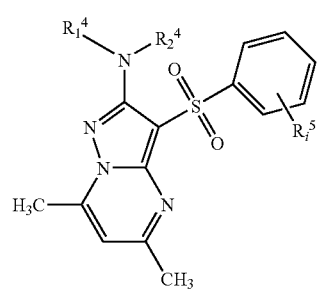

wherein:
$R^4_1$ and $R^4_2$ are all as defined above;
$R^5_i$ represents one or two optionally identical substituents selected from hydrogen, lower alkyl, trifluoromethyl or halogen.

3. The compound of claim 2, selected from the group, representing 5,7-dimethyl-2-methylamino-3-(phenylsulfonyl)pyrazolo[1,5-a]pyrimidine, 5,7-dimethyl-2-dimethylamino-3-(phenylsulfonyl)pyrazolo[1,5-a]pyrimidine, 5,7-dimethyl-2-methylamino-3-(4-fluorophenylsulfonyl)pyrazolo[1,5-a]pyrimidine, 5,7-dimethyl-2-dimethylamino-3-(4-fluorophenylsulfonyl)pyrazolo[1,5-a]pyrimidine, 5,7-dimethyl-2-methylamino-3-(3-fluorophenylsulfonyl)pyrazolo[1,5-a]pyrimidine, 5,7-dimethyl-2-dimethylamino-3-(3-fluorophenylsulfonyl)pyrazolo[1,5-a]pyrimidine, 5,7-dimethyl-2-methylamino-3-(3-chlorophenylsulfonyl)pyrazolo[1,5-a]pyrimidine, and 5,7-dimethyl-2-dimethylamino-3-(3-chlorophenylsulfonyl)pyrazolo[1,5-a]pyrimidine, or pharmaceutically acceptable salt thereof.

4. A pharmaceutical formulation for prophylaxis and treatment of various condition and disease of CNS of human and warm blooded animal, pathogenesis of which is associated with $5\text{-}HT_6$ receptors, comprising a pharmaceutically effective amount of a compound of formula 1, or pharmaceutically acceptable salt thereof, according to claim 1 and pharmaceutically acceptable carriers, including inert excipients and/or solvents.

5. The pharmaceutical formulation according to claim 4, which is in the form of tablet, capsule, or injection placed in pharmaceutically acceptable packing.

* * * * *